United States Patent [19]
Padhye et al.

[11] Patent Number: 5,658,548
[45] Date of Patent: Aug. 19, 1997

[54] NUCLEIC ACID PURIFICATION ON SILICA GEL AND GLASS MIXTURES

[75] Inventors: Vikas V. Padhye; Chuck York, both of Madison, Wis.; Adam Burkiewicz, Gdansk, Poland

[73] Assignee: Promega Corporation, Madison, Wis.

[21] Appl. No.: 476,849

[22] Filed: Jun. 7, 1995

Related U.S. Application Data

[63] Continuation-in-part of Ser. No. 115,504, Aug. 30, 1993, abandoned.

[51] Int. Cl.$^6$ .............................. C03C 1/00; C03C 12/00; C01B 33/12; C01B 33/14
[52] U.S. Cl. ..................... 423/335; 536/25.42; 435/91.1; 428/406
[58] Field of Search .......................... 435/91.1; 423/335; 501/32, 53; 536/25.4, 25.41, 25.42; 428/406

[56] References Cited

U.S. PATENT DOCUMENTS 5,075,430  12/1991  Little.
5,155,018  10/1992  Gillespie et al..

OTHER PUBLICATIONS

Boom, et al., "Rapid and Simple Method for Purification of Nucleic Acids", *Journal of Clinical Microbiology*, vol. 28, No. 3, pp. 495–503, 1990.

Marko, et al., "A Procedure for the Large–Scale Isolation of Highly Purified Plasmid DNA Using Alkaline Extraction and Binding to Glass Powder", *Analytical Biochemistry*, vol. 121, pp. 382–387, 1982.

Chen, et al., "Recovery of DNA Segments from Agarose Gels", *Analytical Biochemistry*, vol. 101, pp. 339–341, 1980.

Vogelstein, et al., "Preparative and analytical purification of DNA from agarose", *Proc. Natl. Acad. Sci.*USA, vol. 76, No. 2, pp. 615–619, 1979.

*Primary Examiner*—Gary L. Kunz
*Attorney, Agent, or Firm*—Foley & Lardner

[57] ABSTRACT

The present invention provides compositions and methods for isolating nucleic acids with lengths greater than about 50 bases, from cells, gels, solutions and other media, in which nucleic acids occur in vivo or in vitro. The compositions of the invention are mixtures of the silica materials silica gel and glass particles, particularly glass microfibers; such mixtures combined with chaotropic salts, such as guanidinium chloride or guanidinium thiocyanate; and suspensions of such mixtures in aqueous solutions of chaotropic salts. In the methods of the invention, an aqueous solution comprising nucleic acid is mixed with an aqueous solution of chaotropic salts and the resulting solution is contacted with a mixture of the silica materials, whereupon the nucleic acid in the solution binds to the silica materials. The chaotropic salts and components, other than the nucleic acid adsorbed to the silica materials, from the aqueous solution treated by the method of the invention are washed from the silica materials. Finally, the nucleic acid can be obtained by elution from the silica materials. The methods provide nucleic acid in water or buffer, such as TE buffer, free of contamination by any salt or macromolecule that would interfere with further processing or analysis.

30 Claims, No Drawings

NUCLEIC ACID PURIFICATION ON SILICA GEL AND GLASS MIXTURES

This application is a continuation-in-part of U.S. patent application Ser. No. 08/115,504, filed Aug. 30, 1993, entitled NUCLEIC ACID PURIFICATION COMPOSITIONS AND METHODS, now abandoned.

TECHNICAL FIELD

The present invention relates to compositions and methods for separating nucleic acids from other substances, with which nucleic acids are combined in vivo and in vitro, and isolating nucleic acids in condition for further processing or analysis.

BACKGROUND OF THE INVENTION

The application of molecular biological techniques, such as reverse transcription, cloning, restriction analysis, sequencing, or the like to nucleic acids, including RNAs and DNAs, requires that the nucleic acids be provided substantially free of certain contaminants. Such contaminants include, among others, substances that block or inhibit chemical reactions, including nucleic acid hybridizations, enzymatically catalyzed reactions, and other types of reactions, used in molecular biological techniques; substances that catalyze the degradation or depolymerization of a nucleic acid of interest; or substances that provide "background" indicative of the presence in a sample of a quantity of a nucleic acid of interest when the quantity is in fact not present in the sample. These contaminants include macromolecular substances, such as enzymes, other types of proteins, polysaccharides, or polynucleotides, as well as lower molecular weight substances, such as lipids, low molecular weight enzyme inhibitors or oligonucleotides.

The problem of obtaining DNA or RNA of interest sufficiently free of contaminants for application of molecular biological methods is complicated by the complex systems in which the DNA or RNA is typically found. These systems, such as cells from tissues, cells from body fluids such as blood, lymph, milk, urine, feces, semen, or the like, cells in culture, agarose or polyacrylamide gels, or solutions in which target nucleic acid amplification has been carried out, typically include significant quantities of contaminants from which the DNA or RNA of interest must be removed intact before being subjected to a molecular biological procedure.

Conventional protocols for obtaining DNA or RNA from cells are well known in the art and are described in, for example, Chapter 2 (DNA) and Chapter 4 (RNA) of F. Ausubel et al., eds., Current Protocols in Molecular Biology, Wiley-Interscience, New York (1993). For DNA, these protocols generally entail gently lysing the cells with solubilization of the DNA and enzymatically or chemically substantially freeing the DNA from contaminating substances such as proteins, RNA and other substances (i.e., reducing the concentrations of these contaminants in the same solution as the DNA to a level that is low enough that the molecular biological procedures of interest can be carried out). For isolation of RNA, the lysis and solubilization procedures must include measures for inhibition of ribonucleases and contaminants to be separated from the RNA including DNA.

The protocols also generally entail use of phenol/chloroform extraction (i.e., extraction with phenol/chloroform or phenol/chloroform/isoamyl alcohol) and ethanol (or isopropanol) precipitation (to obtain DNA) that is substantially free of contaminants that would interfere with molecular biological procedures with the DNA. However, phenol/chloroform extractions have significant drawbacks. Among these drawbacks are the time required for the multiple steps necessary in the extractions and the dangers of using phenol or chloroform. Phenol causes severe burns on contact. Chloroform is highly volatile, toxic and flammable. These dangers require that phenol be handled and phenol/chloroform extractions be carried out in a fume hood. Another undesirable characteristic of phenol/chloroform extractions is that the oxidation products of phenol can damage nucleic acids. Only freshly redistilled phenol can be used effectively, and nucleic acids cannot be left in the presence of phenol. Generally also, multi-step procedures are required to isolate RNA after phenol/chloroform extraction. Ethanol (or isopropanol) precipitation must be employed to precipitate the DNA from a phenol/chloroform-extracted aqueous solution of DNA and remove residual phenol and chloroform from the DNA. Further, ethanol (or isopropanol) precipitation is required to remove some nucleoside triphosphate and short (less than about 30 bases or base pairs) single or double-stranded oligonucleotide contaminants from the DNA.

There is a need recognized in the art for methods, that are simpler, safer, or more effective than phenol/chloroform extraction/ethanol precipitation to purify DNA sufficiently for manipulation using molecular biological procedures.

There further is a need in the art for improved methods of isolation of RNA to a purity sufficient for manipulation.

Fractionation according to size of DNA recovered from cells is required for many molecular biological procedures, and such fractionation is typically accomplished by agarose or polyacrylamide gel electrophoresis. For analysis or treatment by a molecular biological procedure after fractionation, the DNA in the fraction(s) of interest must be separated from contaminants, such as agarose, other polysaccharides, polyacrylamide, acrylamide, or acrylic acid, in the gel used in such electrophoresis. Thus, there is a need in the art for methods to accomplish such separations.

Methods for amplifying nucleic acids or segments thereof, such as the well known polymerase chain reaction (PCR) process (see, e.g., U.S. Pat. No. 4,683,202), yield solutions of complex mixtures of enzymes, nucleoside triphosphates, oligonucleotides, and other nucleic acids. Typically, the methods are carried out to obtain an highly increased quantity of a single nucleic acid segment ("target segment"). Often it is necessary to separate this nucleic acid from other components in the solution after the amplification process has been carried out. There is a need in the art for simple methods to accomplish these separations.

A particular problem in this regard that sometimes arises in amplifications by the PCR method is the problem of separating the nucleic acid (usually double-stranded DNA) intended to be amplified in the process from "primer dimers," that also might be amplified to a high level in the process. "Primer dimers" are DNAs which result from priming of DNA synthesis by one of the primers used in a PCR amplification on another primer as a template. Primer dimers can amplify to high concentrations in PCR amplifications.

Silica materials, including glass particles, such as glass powder, silica particles, and glass microfibers prepared by grinding glass fiber filter papers, and including diatomaceous earth have been employed in combination with aqueous solutions of chaotropic salts to separate DNA from other substances and render the DNA suitable for use in molecular biological procedures by substantially freeing the DNA of contaminants that would impair or prevent its being employed in such procedures. See U.S. Pat. No. 5,075,430 and references cited therein, including Marko et al., Anal. Biochem. 121, 382–387 (1982) and Vogelstein et al., Proc. Natl. Acad. Sci. (USA) 76, 615–619 (1979). See also Boom et al., J. Clin. Microbiol. 28, 495–503 (1990). With reference to intact glass fiber filters used in combination with aqueous solutions of a chaotropic agent to separate DNA from other substances, see Chen and Thomas, Anal. Biochem. 101, 339–341 (1980). Vogelstein et al., supra, suggest that silica gel is not suitable for use in DNA separations. With regard to separation of RNA using silica materials and chaotropic agents, see Gillespie et al., U.S. Pat. No. 5,155,018.

Prior to the present invention, mixtures of glass particles and silica gel, such mixtures in suspension in aqueous solutions of chaotropic agents, and the use of such suspensions to separate DNA or RNA from other substances or isolate DNA or RNA so separated were not known.

SUMMARY OF THE INVENTION

It has now been discovered that a mixture of silica gel and glass particles in combination with an aqueous solution of chaotropic salts is advantageously used to separate DNA or RNA from other substances, to render the DNA or RNA sufficiently free of contaminants to be suitable for use in molecular biological procedures, and isolate the DNA or RNA for such uses. Such a mixture may also be employed advantageously to separate and isolate RNA.

Thus, the present invention provides mixtures of silica gel and glass particles, combinations of these mixtures with chaotropic salts and aqueous solutions of chaotropic salts, suspensions of the mixtures of silica gel and glass particles in aqueous solutions of chaotropic salts, and methods of using such combinations and suspensions in separating DNA or RNA from aqueous solutions which comprise same and isolating DNA or RNA that has been so separated. These methods of use of the invention are surprising improvements of methods of using, in combination with chaotropic salts or in suspension in aqueous solutions of chaotropic salts, of diatomaceous earth alone or glass particles alone in such separations and isolations of DNA or RNA.

DETAILED DESCRIPTION OF THE INVENTION

In one of its aspects, the invention is a mixture of silica gel and glass particles.

In another of its aspects, the invention entails a suspension of silica gel and glass particles in an aqueous solution, which comprises one or more chaotropic salts.

In still another aspect, the invention is a method of separating DNA or RNA from a first aqueous solution comprising the DNA or RNA, which method comprises (1) preparing a second aqueous solution by mixing an aliquot of said first aqueous solution with a third aqueous solution, which comprises one or more chaotropic salts; and (2) contacting an aliquot of said second aqueous solution with a mixture of silica gel and glass particles.

The method of the invention for separating DNA or RNA from an aqueous solution comprising same becomes a method of the invention for isolating DNA or RNA by adding to the method of separating, after step (2) thereof, the following steps: (3) separating from a first portion of the mixture of silica gel and glass particles, which was contacted in step (2) with said aliquot of second solution, substantially all of said aliquot which is not bound to said first portion of said mixture; (4) washing a second portion of said mixture of silica gel and glass particles, which is a portion of said first portion of said mixture, with a fourth aqueous solution which is effective to remove substantially all of the chaotropic ions, but substantially ineffective in removing DNA (or RNA as the case may be) other than short oligonucleotides, from said second portion of said mixture of silica gel and glass particles; and, after step (4), (5) washing a third portion of said mixture of silica gel and glass particles, which is a portion of said second portion of said mixture, with water or a fifth aqueous solution to elute DNA (or RNA as the case may be) from said third portion. The DNA or RNA eluted in the fifth step is DNA or RNA isolated in accordance with the invention and is suitable for use without further purification in molecular biological procedures.

The term "silica materials," as used in the present specification, means silica gel or glass particles, as both are mostly silica.

Silica gel employed in the present invention is conventional silica gel, preferably of at least "chromatography grade".

Silica gel is widely available commercially. Silica gel can be characterized by "pore diameter," "particle size" and specific surface area. For the present invention silica gel is suitable which has a pore diameter between about 30 and about 300 Angstrom units, with about 60 Angstrom units being preferred, a particle size between about 5 µm and about 300 µm, with about 10 µm being preferred, and a specific surface area of between about 100 m$^2$/g and about 1000 m$^2$/g, with about 500 m$^2$/g being preferred. The most preferred silica gel for the invention has a pore diameter of about 60 Angstroms, a particle size of 9–11 µm, and a specific surface area between about 450 and 550 m$^2$/g.

The term "glass particles" in the present specification means particles of crystalline silicas (e.g., α-quartz, vitreous silica), even though crystalline silicas are not formally "glasses" because they are not amorphous, or particles of glass made primarily of silica. The glass particles will generally be at least 75% by weight SiO$_2$ and may include other components typical of common silica-based glasses, such as sodium oxide, potassium oxide, aluminum oxide, boron oxide, calcium oxide, or the like. The compositions of the glass particles are such that the particles remain solid or solid-like, like α-quartz, ordinary soda-lime glasses, or borosilicate glasses (such as Pyrex®), up to at least 100° C. and between about 10$^{-3}$ atm. and a few atmospheres pressure and in all of the aqueous solutions, with which they are employed in accordance with the present invention, under all of the conditions to which such solutions are subjected in separating or isolating DNA in accordance with the invention. Similarly, glass particles in the silica mixtures of the invention, similar to α-quartz, ordinary soda-lime glasses, or borosilicate glasses, are essentially insoluble in the aqueous solutions, with which the particles are employed in accordance with the present invention, under all of the conditions to which such solutions are subjected in separating or isolating DNA in accordance with the invention. This "essential insolubility" comprehends that, as with ordinary glasses, there may be a minor amount of leaching, that is inconsequential with respect to carrying out the methods of the present invention, of components from glass particles.

Glass particles include ground, crystalline silica powders; glass powders, including soda-lime and borosilicate glass powders, which can be obtained by pulverizing the glasses; and glass microfibers, which can be obtained by pulverizing glass fibers, including such fibers obtained from glass-fiber filters, as described hereinbelow. Glass microfibers obtained as described below are preferred. With respect to the use, with chaotropic salt solutions, of glass particles in DNA separations and sizes for such particles, see Boom et al., J. Clin. Microbiol. 28, 495–503 (1990); Marko et al., Anal. Biochem. 121, 382–387 (1982); and Vogelstein et al., Proc. Natl. Acad. Sci. (USA) 76, 615–619 (1979).

Silica gels or glass particles, which are purchased as chromatography grade or better, may be used without further purification in mixtures or suspensions of the invention, although they, like particles of lesser purity, may be washed prior to such use.

Although, in the mixtures of the invention, the weight ratio of silica gel to glass particles may range from 1:1 to 100:1, a more preferred range is about 5:1 to about 50:1, and the most preferred range for DNA is about 10:1 (about 9:1 to about 11:1), while for RNA it is about 30:1 (about 25:1 to 35:1).

The mixtures of the invention, of silica gel and glass particles, are prepared by simply admixing the silica gel, dry or in suspension in a liquid, with the glass particles, which also may be dry or in suspension in a liquid. Similarly, the mixtures of the invention of silica gel, glass particles and chaotropic salts are prepared by simply admixing the components, which may be dry, in suspension in a liquid or, in the case of the salts, in solution. The preferred "liquids" for suspensions or for solutions of the chaotropic salts are water or aqueous solutions.

The pH of the resin made with distilled water is between 5.5 to 6.5, due to the presence of the guanidinium salt. The pH of the resin can be changed by adding buffer, for example, pH 4.0–5.0 upon addition of citrate, pH 5.5–6.5 upon addition of acetate or pH 7.0–9.0 upon addition of Tris, to the preparation in place of pure water.

Reference to a mixture or suspension of silica gels and glass particles "consisting essentially of" silica gel and specified type(s) of glass particles (e.g., glass microfibers) means that essentially the only silica materials in the mixture are silica gel and the specified type(s) of glass particles. In such a mixture or suspension, there may be types of materials (e.g., water, buffer, salts) other than silica materials and, among the silica materials, there might be insignificant amounts of non-essential or insignificant components, such as impurities.

Chaotropic salts are salts of chaotropic ions. The salts are highly soluble in aqueous solutions. The chaotropic ions provided by such salts, at sufficiently high concentration in aqueous solutions of proteins or nucleic acids, cause proteins to unfold, nucleic acids to lose secondary structure or, in the case of double-stranded nucleic acids, melt (i.e., strand-separate). It is thought that chaotropic ions have these effects because they disrupt hydrogen-bonding networks that exists in liquid water and thereby make denatured proteins and nucleic acids thermodynamically more stable than their correctly folded or structured counterparts. Chaotropic ions include guanidinium, iodide, perchlorate and trichloroacetate. Preferred in the present invention is the guanidinium ion. Chaotropic salts include guanidinium chloride, guanidinium thiocyanate (which is sometimes referred to as guanidinium isothiocyanate), sodium iodide, sodium perchlorate, and sodium trichloroacetate. Preferred are the guanidinium salts.

In the aqueous, chaotropic salt solutions used in the present invention to contact silica materials or prepare suspensions of such materials, the concentration of chaotropic ions is preferably above about 2M. In such a solution, before DNA is introduced into it by mixing with an aqueous solution comprising DNA, the concentration of chaotropic ions is preferably above about 4M, and more preferably above about 5M. Further, the ratio of the volume of such a solution of chaotropic salt (prior to introduction of DNA or RNA) to the volume of aqueous solution of DNA or RNA, with which the solution of chaotropic salt is combined in carrying out the DNA separation methods of the invention, is preferably greater than 1. For RNA separation methods, it is preferably about 4:1 (3:1 to 5:1).

Thus, in the suspensions of the invention, comprising silica gel and glass particles in an aqueous solution of chaotropic salts, prior to being combined with a DNA or RNA solution from which DNA or RNA, respectively, is to be separated, the concentration of guanidinium chloride, if that is the chaotropic salt, is preferably 6M to 8M and the concentration of guanidinium thiocyanate, if that is the chaotropic salt, is preferably 5M to 7M.

A problem that has been found with compositions comprising silica gel, glass particles and an aqueous guanidinium thiocyanate solution is that the compositions acquire a yellow color, clearly noticeable to the naked eye, within a few days after being made. Such coloration is commercially unacceptable. In connection with the present invention, it has been found surprisingly and unexpectedly that coloration of these compositions can be avoided by including in them a chelating agent such as citrate, EGTA or EDTA. Preferred in this regard are EDTA or EGTA at between about 5 mM and about 15 mM in the solution of the composition. Preferred for providing the EDTA to the solution is the disodium salt of EDTA. Further, it has been found surprisingly that coloration of a suspension of the invention which comprises guanidinium thiocyanate can be avoided by washing, with a chelating-agent-containing solution, the solids (silica materials) to be employed in making the suspension.

With any chaotropic salt used in the invention, it is desirable that the concentration of the salt, in any of the solutions in which the salt is employed in carrying out the invention, remain below the solubility of the salt in the solution under all of the conditions to which the solution is subjected in carrying out the invention.

The compositions and methods of the invention are especially suitable for separating or isolating DNAs with lengths of between about 50 bases and about 50–60 kilobases from other components. The compositions and methods of the invention are also suitable for separating or isolating RNAs of virtually any length that occur naturally, in cells, viruses or the like. Thus, the methods are suitable, for example, for separating vector DNA (e.g., plasmid DNA, lambda DNA) from genomic DNA and for separating PCR-amplified target or analyte DNA, of length greater than about 200 bases, from primer or primer-dimer DNA, of significantly shorter length (typically about 20–about 100 bases in length). The DNAs may be provided for the methods in any form, including linear, circular, single-stranded, double-stranded, or partially double-stranded.

In defining the methods of the invention, reference to an "aliquot" of a solution is to all or some part of the volume of the solution and reference to a "portion" of a mixture of silica gel and glass particles is to all or some part of the mass of the mixture.

The first step in the methods of the invention for separating or isolating DNA or RNA is to combine an aliquot of aqueous solution comprising the DNA or RNA to be separated or isolated (a first solution) with an aqueous solution of a chaotropic salt (a third solution) to make a second solution and then the second step, which may occur simultaneously with the first, is to contact an aliquot of the second solution with a mixture of silica gel and glass particles. The concentration of chaotropic ion in the second solution is preferably at least 2M, such that, if that concentration in the third solution is no more than 4M, the volume of the second solution is preferably less than twice that of the third solution.

The mixture of silica gel and glass particles will preferably be uniform (i.e., the silica gel particles and glass particles will be intermingled as evenly as possible throughout the mixture). The mixture may be dry, packed in a column or embedded in a membrane, and contact with the second solution accomplished by passing that solution through the column or membrane. See, e.g., U.S. Pat. No. 5,075,430. More preferably, the first and second steps of the methods will be accomplished simultaneously by combining the aliquot of aqueous solution comprising the DNA or RNA with a suspension of the invention of silica gel and glass particles in an aqueous solution of chaotropic salts.

The DNA or RNA, separated or isolated by a method of the invention, can be obtained from virtually any source of DNA or RNA. There might be processing, prior to carrying out the method of the invention, to provide the aqueous solution of DNA or RNA on which the method of the invention is carried out. Thus, the DNA or RNA can be from eukaryotic or prokaryotic cells in culture or from cells taken or obtained from tissues, multicellular organisms including animals and plants; body fluids such as blood, lymph, urine, feces, or semen; embryos or fetuses; food stuffs; cosmetics; or any other source of cells. The DNA or RNA can include DNA or RNA of organelles, viruses, phages, plasmids, viroids or the like that infect cells. Cells will be lysed and the lysate usually processed in various ways familiar to those in the art to obtain an aqueous solution of DNA or RNA, to which the separation or isolation methods of the invention are applied. The DNA or RNA, in such a solution, will typically be together with other components, such as proteins, RNAs (in the case of DNA separation), DNAs (in the case of RNA separation), or other types of components.

Another example of DNA that can be treated by the methods of the invention is DNA in a solution after an amplification process, such as PCR, is carried out with the solution; usually such solutions will be used directly in the methods of the invention.

Another example of DNA treated by the methods of the invention is DNA obtained from size-fractionating gels, such as agarose or polyacrylamide gels. In preparing the aqueous solution of DNA for application of the methods of the invention, the DNA will be separated from the gel matrix, such as by eluting the DNA from a slice of the gel into a solution or by melting or otherwise degrading the gel or a slice thereof in a solution.

In the methods, after the first two steps have been carried out, the DNA or RNA has been separated by binding to the silica material. Further steps are necessary to isolate the separated DNA or RNA so that it can be employed without need for further purification in molecular biological procedures.

A third step is carried out to separate from at least a portion (and typically all) of the silica materials (with bound DNA or RNA) substantially all of the aliquot of the second solution which was combined with the silica materials for the DNA or RNA separation but not bound to said portion of the silica materials. This separation of substantially all of this aliquot of second solution can be accomplished, when the second solution/silica material combination is held in a column (as described in the examples) or between membranes (see U.S. Pat. No. 5,075,430), in part simultaneously with the fourth step, described below, by layering fourth solution on top of the silica materials/second solution combination in the column and using a vacuum at room temperature to suction fluid of the second solution away from, and fourth solution through and away from, the silica materials. Alternatively, the fluid of the second solution could be suctioned away from the silica materials before the fourth step is started. In another alternative, the second solution/silica materials combination could be centrifuged and the supernatant thoroughly removed from the pellet before the fourth step is started with the pellet. The separation of fluid of the second solution from the silica materials should be accomplished with evaporating the fluid to dryness. As the skilled will recognize, this process of separating the silica materials from components of second solution not bound thereto will remove most of the chaotropic salt(s), proteins and other contaminants which do not bind strongly to the silica materials.

However, to remove enough of these contaminants, as well as others that bind with some tenacity to the silica materials, there is a fourth step in the isolation method of the invention. This step entails washing with a fourth aqueous solution a portion (typically all) of the silica materials, to which the DNA or RNA of interest is bound and from which substantially all of the unbound components of the second solution had been removed. This fourth aqueous solution has a volume and composition to be effective in removing substantially all of the chaotropic ions, but substantially ineffective in removing DNA or RNA other than short oligonucleotides (shorter than about 200 nucleotides, although it is possible at lower yields to separate DNAs or RNAs as short as about 40 bp with the methods of the invention), from the portion of silica materials washed with the fourth solution. Typically, besides being effective to remove chaotropic salt(s) left behind in removal of fluid of the second solution, the fourth solutions are also effective to remove protein and short oligonucleotides left behind in that removal. As will be apparent to the skilled, this solution should not significantly elute DNA or RNA from the silica materials. Many wash solutions suitable for this washing step of the method of the invention are known in the art. Typically these solutions will be aqueous solutions of between about 20% by volume and about 95% by volume of an alkanol, which has 1 to 4, and preferably 2 or 3, carbons in the alkyl moiety. The solutions may also include other components, such as, for example, 0.05M–0.20M either NaCl or KOAc; low concentrations of buffer, such as 5 mM–20 mM Tris-HCl, to maintain the pH nearly neutral, and low concentrations of chelators, such as 0.1 mM–5 mM EDTA, EGTA, CDTA or the like.

Any standard washing procedure can be employed in the fourth step. As indicated above, the fourth step can be carried out at least in part simultaneously with the third step. As indicated in the examples, when fourth solution is pulled through and from the silica materials by vacuum, it is preferred to centrifuge the silica materials including residual fourth solution to remove residual fourth solution from the silica materials without evaporating the fourth solution to dryness. If the silica materials are in a chromatography column, a suitable volume of the fourth solution can be passed through the material in the column to substantially completely remove the chaotropic salts and other contaminants of concern. In another procedure, which can be repeated as often as necessary to substantially completely remove chaotropic salts and other contaminants of concern, the silica materials can be suspended in the fourth solution and then separated from the solution by pelleting by centrifugation and removing the supernatant from the pellet. It is preferred that, before the fifth step, substantially all of the fourth solution be separated from the silica materials without evaporating the fourth solution to dryness, e.g., by centrifugation, as illustrated in the examples.

In the fifth step of the process of the invention for isolating DNA or RNA, a portion of the silica materials, with the separated DNA or RNA bound thereto and after being washed with the fourth solution as described above, is washed with water or a fifth solution that elutes the DNA or RNA from the materials. The isolated DNA or RNA is then in solution in the water or fifth aqueous solution. The washing can be accomplished by any of various methods well known in the art, such as passing, by centrifugation, application of pressure, or pulling with a vacuum, the fifth solution through a column holding the silica materials with the bound DNA or RNA. The fifth aqueous solution will be "low salt" (i.e., have a low ionic strength, less than about twice that of the TE buffer described in the Examples below), and will preferably be buffered to a pH between about 6.5 and 8.5, more preferably 7.0 to 8.0. A particularly preferred fifth aqueous solution for use in the methods of the invention for isolating DNA or RNA is the TE buffer, which is well known in the art.

As indicated in the Examples, DNA or RNA isolated in accordance with the invention using TE buffer can be stored in the buffer until use.

"Substantially all," "substantially completely," "substantially ineffective" and like terms, in the context of the description of the methods of the invention, are necessarily operationally defined and mean sufficiently to yield, after the elution in the fifth step, separated DNA or RNA that is suitable for a molecular biological procedure of interest to be carried out on it. The skilled in the art are able to determine readily what is required, in terms of volumes and compositions of washing solutions and washing procedures, to obtain such separated DNA by the methods of the invention.

As indicated above, unexpectedly the DNA and RNA separation and isolation methods of the invention, which employ a mixture of silica materials comprising silica gel and glass particles, are more efficient, in the recovery of DNA and RNA, respectively, than prior art methods.

The eluted DNA or RNA, provided by the method of the invention for isolating DNA or RNA, respectively, is suitable, without further purification, for analysis or further processing by molecular biological procedures. The eluted nucleic acid can be analyzed by, for example, sequencing, restriction analysis, or nucleic acid probe hybridization. Thus, the methods of the invention can be applied as part of methods, based on analysis of DNA or RNA, for, among other things, diagnosing diseases; identifying pathogens; testing foods, cosmetics, blood or blood products, or other products for contamination by pathogens; forensic testing; paternity testing; and sexing of fetuses or embryos.

The eluted DNA or RNA provided by the method of the invention can be processed by any of various exonucleases and endonucleases that catalyze reactions with DNA or RNA, respectively, and, in the case of DNA, can be digested with restriction enzymes, which cut at restriction sites present in the DNA. Restriction fragments from the eluted DNA can be ligated into vectors and transformed into suitable hosts for cloning or expression. Segments of the eluted DNA or RNA can be amplified by any of the various methods known in the art for amplifying target nucleic acid segments. If eluted DNA is a plasmid or another type of autonomously replicating DNA, it can be transformed into a suitable host for cloning or for expression of genes on the DNA which are capable of being expressed in the transformed host. Plasmid DNAs isolated by methods of the present invention have been found to be more efficiently transfected into eukaryotic cells than those isolated by the prior art method, wherein diatomaceous earth is employed in place of the silica gel in the methods of the invention of this application.

The following, non-limiting examples teach various embodiments of the invention. In the examples, and elsewhere in the specification and claims, volumes and molarities are at room temperature unless specified otherwise.

EXAMPLE 1

Preparation of Suspension with Guanidinium Chloride

A 7M guanidine-HCl (i.e., guanidinium chloride) solution was prepared by dissolving 20 kg of ultrapure guanidine-HCl (Amresco Ultrapure, from Amresco, Cleveland, Ohio, USA) in 30 L of deionized distilled water.

Glass particle (i.e., in this example, glass microfiber) for the resin was then prepared as follows: Sixty-three (63) 12.5 cm glass-fiber filters, with a total mass of approximately 41.7 gms., (Whatman GF/A, Catalog No. 1820-125, widely available from Whatman through numerous distributors of laboratory and scientific apparatus) were cut into quarters. The filters were then added gradually to 6 L of 5M NaCl or distilled water while dispersing with a polytron on medium to high speed. After all of the filters had been added, they were homogenized to an uniform sludge with no visible paper remaining; this homogenization lasted about 5 minutes. The sludge was then collected in a Buchner funnel and washed with about 24 L of deionized distilled water.

Although Whatman GF/A filters are specified in the instant example, Whatman GF/B, GF/C and GF/F filters are also suitable, as are any glass fiber filters having binders which are removable by the glass-microfiber preparation process described herein.

The suspension (alternatively referred to herein as a "resin" or a "slurry") was then made as follows: The 41.7 g of washed, glass-microfiber sludge and 450 g of silica gel 60-10 (pore size 60 Angstrom, particle size 9–11 μm, W. R. Grace, Davison Chemical Division, Baltimore, Md., USA) were added to the 30 L of 7M guanidine-HCl solution.

Although silica gel 60-10 is preferable, the following silica gel are also acceptable. Silica gel with pore size 60 Angstrom, particle size 30 μm or 105 μm; silica gel with pore size 100 Angstrom, particle size 30 μm or 105 μm; silica gel with pore size 250 Angstrom, particle size 30 μm or 50 μm; silica gel Grade 22 with pore size 100 Angstrom, particle size 70–200 μm; silica gel Grade 62 with pore size 60 Angstrom, particle size 70–200 μm.

The resulting mixture was stirred until an uniform suspension was obtained. This suspension a suspension of the invention.

The pH of the uniform suspension was 5.5, and the conductivity of a suspension resulting from mixing 10 μl of resin in 10 ml of deionized distilled water was 1150 μmhos.

Although the ratio of silica gel:glass fiber filter paper used to prepare the suspension of the present example is approximately 10:1 by weight, ratios in the range of 5:1 to 20:1 are acceptable.

In a series of experiments with different suspensions, each of which was prepared as described in this Example except that the amount of the silica gel was varied from 1 g/L of guanidinium chloride solution to 20 g/L of guanidinium salt solution, it was found that the suspension that was most efficient in recovering DNA from an aqueous solution thereof was the suspension described in the present Example, with 15 g/L of guanidium chloride solution.

After the stirring, material settles quite rapidly from the suspension on standing. Immediately prior to use, the uniform suspension (resin) must be re-established by thoroughly stirring or mixing settled material with the supernatant.

EXAMPLE 2

Preparation of Resin with Guanidium Thiocyanate

To prepare the title resin of this Example, the procedure of Example 1 was followed except that a 6M solution of guanidinium thiocyanate (crystallized, Amresco Ultrapure, from Amresco, Cleveland, Ohio, USA) was used in place of 7M guanidine-HCl. The guanidinium thiocyanate was stabilized against discoloration by adding EDTA (EDTA disodium salt, Sigma Chemical Company, St. Louis, Mo., USA) to a final concentration of 10 mM.

The use of guanidinium thiocyanate is preferred when using the present invention to isolate nucleic acid fragments from agarose and other gels because it efficiently dissolves both high melting point and low melting point agarose compositions.

EXAMPLE 3

Plasmid Purification Protocol

This example describes standard plasmid isolation procedures using the resin of Example 1 starting from a 1–3 ml culture of E. coli.

A. Composition of Buffers
1. Cell Resuspension Solution:
   50 mM Tris-HCl, pH 7.5
   10 mM EDTA
   100 μg/ml RNase A (ribonuclease A)(DNase-free)
2. Column Wash Solution:
   (a)
      (i) 200 mM NaCl, 20 mM Tris-HCl, 5 mM EDTA, pH 7.5; or
      (ii) 190 mM KOAc, 20 mM Tris-HCl, 0.1 mM EDTA, pH 7.5
   (b) Dilute (a) 1:1.4 with 95% EtOH (ethanol)
3. TE Buffer:
   10 mM Tris-HCl, pH 7.5
   1 mM EDTA
4. Neutralization Solution:
   1.32M KOAc (potassium acetate), pH 4.8
5. Cell Lysis Solution:
   0.2M NaOH
   1% SDS (sodium dodecyl sulfate)

B. Production of a Cleared Lysate
1. Pellet 1–3 ml of cells by centrifugation for 1–2 minutes at top speed in a microcentrifuge. Resuspend the cell pellet in 200 μl of Cell Resuspension Solution. Transfer the resuspended cells to a microcentrifuge tube.
2. Add 200 μl of Cell Lysis Solution and mix by inverting the tube several times. The cell suspension will clear almost immediately. If it does not, continue inverting until it clears.
3. Add 200 μl of Neutralization Solution and mix by inverting the tube several times.
4. Spin in a microcentrifuge at top speed for 5 minutes.
5. Decant the cleared supernatant to a new microcentrifuge tube. The cleared supernatant is an aqueous solution comprising DNA, from which DNA can be separated or isolated by a method of the invention.

If a vacuum manifold is available, proceed with section C. If no vacuum manifold is available, proceed with section D.

C. Plasmid Purification Using a Vacuum Manifold
1. Add 1 ml of the resin of Example 1 to the supernatant from Step B.5 and mix by inverting the tube. Thoroughly mix the resin of Example 1 before removing an aliquot. If necessary, warm the resin to 25°–37° C. (less than or equal to 10 minutes) to dissolve any crystals. Do not use the resin above 30° C. Although there is some settling of the silica gel resin, the fine particle size of the silica gel results in the particles remaining suspended in the solution for a longer period of time than a resin devised of diatomaceous earth rather than silica gel.
2. For each plasmid miniprep, a Wizard™ Miniprep mini-column is used. For larger preparations, a Wizard™ Midiprep, Wizard™ Maxiprep or Wizard™ Megaprep columns can be used. Wizard™ Miniprep, Wizard™ Midiprep, Wizard™ Maxiprep and Wizard™ Megaprep columns are available from Promega Corp., Madison, Wis., USA and are chromatography columns, which are supplied without being packed with chromatographic resin and are designed for convenient use in recovery of nucleic acids from aqueous solutions containing same. The skilled will recognize that similar columns, which are also suitable for use in methods of this invention for separating or isolating nucleic acids, are readily available from sources other than Promega Corp. Although the procedure described here is in terms of using the Wizard™ Miniprep mini-column, the skilled will readily understand how to adapt the procedure to use with larger columns. Remove the plunger from a 3 ml disposable syringe and set aside. Attach the 3 ml disposable luer-lock syringe barrel to the luer-lok extension of each mini-column, and insert the tip of the minicolumn/syringe barrel assembly into the vacuum manifold (e.g., Vac-Man Laboratory Vacuum Manifold, Promega Corp., Catalog No. A7231).
3. Pipet the resin/DNA mixture into the syringe barrel and pull the resin (slurry) into the mini-column by applying a vacuum. After the resin/DNA mixture has entered the column, break the vacuum.
4. Wash the mini-column under vacuum by the addition of 2 ml Column Wash Solution to the syringe barrel, then reapply the vacuum to draw the solution through the mini-column.
5. Dry the resin by continuing the vacuum for an additional 0.5–2 minutes. With reference to the methods of the invention, steps C.4 and C.5 entail the simultaneous separating of "substantially all" of the chaotropic ions (as well as other low molecular weight substances such as nucleotides or short oligonucleotides) from the mixture of silica materials and washing of said mixture of silica materials with a fourth aqueous solution (e.g., of an alkanol) with which proteins are substantially completely eluted from said silica materials.
6. Remove the syringe barrel and transfer the mini-column to a 1.5 ml microcentrifuge tube. Spin the mini-column at top speed in a microcentrifuge for 2 minutes to remove any residual Column Wash Solution.
7. Transfer the minicolumn to a new microcentrifuge tube. Apply to the column 50 μl of water or TE Buffer to the minicolumn and wait 1 minute. For large plasmids (greater than or equal to 10 kb) the use of preheated (65°–70° C.) water or TE buffer may increase yields. For plasmids greater or equal to 20 kb, use 80° C. water or TE buffer.

8. To elute the DNA, spin the mini-column in the microcentrifuge tube at top speed for 0.5–1.0 minute. Remove and discard the mini-column. Plasmid DNA may be stored in the water or TE solution in the microcentrifuge tube at 4° or –20° C. Each isolation can yield as much as 10 µg of plasmid DNA. The yield of plasmid DNA is extremely consistent, when factors affecting yield are held constant (i.e. volume of bacterial culture used (1–3 ml), the copy number of the plasmid and the bacterial strain used). Successive trials each utilizing 1.5 ml of bacteria culture yielded a surprisingly consistent 4.1 µg±0.4 µg of plasmid DNA. Replacing the silica gel with diatomaceous earth resulted in a wide variation in yield, 1.5 ml of bacteria culture resulting in 5.4 µg±1.5 µg of plasmid DNA. The plasmid DNA yielded is in condition for analysis (e.g., restriction analysis, sequencing) or further molecular biological procedures (e.g., transformation, obtaining a particular restriction fragment).

D. Plasmid Purification Using a Disposable Syringe (Without a Vacuum)

1. Add 1 ml of resin of Example 1 to the supernatant from step B.5 and mix by inverting the tube. Thoroughly mix the resin of Example 1 before removing an aliquot. If necessary, warm the resin to 25°–37° C. (less than or equal to 10 minutes) to dissolve any crystals. Do not use the resin above 30° C.

2. For each miniprep, use one mini-column (see Part C above). Remove the plunger from a 3 ml disposable syringe and set aside. Attach the disposable syringe barrel to the luer-lok extension of the mini-column.

3. Pipet the resin/DNA mix into the syringe barrel. Insert the syringe plunger and gently push the slurry into the mini-column with the syringe plunger.

4. Detach the syringe from the mini-column and remove the plunger from the syringe. Reattach the syringe barrel to the mini-column. Pipet 2 ml of Column Wash Solution into the syringe. Insert the syringe plunger into the syringe, and gently push the Column Wash Solution through the mini-column using the syringe plunger.

5. Remove the syringe and transfer the mini-column to a 1.5 ml microcentrifuge tube, and place in a microcentrifuge. Spin the mini-column for 2 minutes at top speed in the microcentrifuge to dry the resin.

6. Transfer the mini-column to a new microcentrifuge tube.

7. To elute the plasmid DNA, apply to the mini-column 50 µl of water or TE buffer to the mini-column and wait 1 minute. For large plasmids (greater than or equal to 10 kb) the use of preheated (65°–70° C.) water or TE buffer may increase yields. For plasmids greater or equal to 20 kb, use 80° C. water or TE buffer.

8. Spin the microcentrifuge tube containing the mini-column for 0.5–1.0 minute in a microcentrifuge. Remove and discard the mini-column. Plasmid DNA may be stored in the microcentrifuge tube at 4° or –20° C. Each isolation can yield as much as 10 µg of plasmid DNA. The yield of plasmid DNA is extremely consistent, when factors affecting yield are held constant (i.e. volume of bacterial culture used (1–3 ml), the copy number of the plasmid and the bacterial strain used). The plasmid DNA yielded is in condition for analysis (e.g., restriction analysis, sequencing) or further molecular biological procedures (e.g., transformation, obtaining a particular restriction fragment).

Notwithstanding the teaching of U.S. Pat. No. 5,075,430 to use sodium perchlorate as a chaotropic salt, and the use of this salt in commercially available kits for DNA purification using diatomaceous earth alone in combination with aqueous solutions of the salt, it has been found that the use of sodium perchlorate, in place of guanidium chloride, as the chaotropic salt in the process described in this Example is undesirable. For reasons that are not clear, a precipitate forms when a sodium perchlorate-containing suspension is mixed with the solution containing DNA from the bacterial lysate. The formation of this precipitate significantly reduces the amount of DNA that can bind to the silica materials and, in the procedures described in this example, clogs the minicolumn when the combination of DNA solution and suspension of silica materials in the chaotropic salt solution is placed in the column. The precipitate advantageously and unexpectedly does not form when guanidinium chloride is used as the chaotropic salt.

EXAMPLE 4

DNA Fragment Isolation from Low Gelling/Melting Temperature Agarose Gels

This example describes a standard DNA-fragment purification protocol using the resin (suspension) of Example 2.

A. Composition of Buffers

Column Wash Solution:

80% (v/v) isopropanol in water.

TE Buffer:

10 mM Tris-HCl, pH 7.5

1 mM EDTA

B. Low Melting/Gelling Agarose Electrophoresis

1. Electrophorese and stain the DNA sample in a low melting/gelling agarose gel using standard protocols. See, e.g., Sambrook et al., Molecular Cloning: A Laboratory Manual, Cold Spring Harbor Laboratory Press, Cold Spring Harbor, N.Y. (1989).

2. Excise the desired DNA fragment using a clean, sterile razor blade or scalpel. Visualize the fragment with a medium or long wavelength UV light, working quickly to minimize the exposure of the fragment to UV light. The fragment should be isolated in ≦300 mg of agarose (approximately 300 µl).

3. Transfer the agarose slice to a 1.5 ml microcentrifuge tube and incubate the sample at 70° C. until the agarose is completely melted, approximately 2 minutes. With reference to the DNA separation/isolation methods of the invention, the melted gel slice, with the DNA, is an example of an aqueous solution comprising DNA to which the methods of the invention can be applied.

C. Fragment Purification Using a Vacuum Manifold

1. Add 1 ml of the resin of Example 2 to the melted agarose slice from Step B.3 and mix by vortexing for 20 seconds.

2. For each gel slice, use one mini-column (See Example 3). Remove the plunger from a 3 ml disposable luer-lock syringe and attach the syringe barrel to the luer-lock extension of each mini-column and insert the tip of the column assembly into the vacuum manifold.

3. Pipet the resin containing the bound DNA into the syringe barrel and pull the resin into the mini-column by applying a vacuum.

4. Wash the mini-column under vacuum by the addition of 2 ml Column Wash Solution to the syringe barrel.

5. Dry the mini-column by continuing the vacuum for an additional 0.5–2 minutes.

6. Remove the syringe barrel and transfer the mini-column to a microcentrifuge tube.

7. Spin the mini-column for 2 minutes to remove any residual Column Wash Solution.

8. Transfer the mini-column to a new microcentrifuge tube.

9. To elute the bound DNA, apply 50 μl of water or TE buffer to the mini-column and wait 1 minute. The DNA will remain intact on the minicolumn for up to 30 minutes.

10. Spin the mini-column in the microcentrifuge tube for 0.5–1.0 minute at 12,000×g. Remove and discard the mini-column. The isolated DNA, ready for analysis or further molecular biological procedures, may be stored in the water or TE solution in the microcentrifuge tube at 4° C. or –20° C.

D. Fragment Purification Using a Disposable Syringe Without a Vacuum

1. Add 1 ml of the resin of Example 2 to the melted agarose slice from Step B.3 and vortex for 20 seconds.

2. For each gel slice, use one mini-column (see Example 3). Remove the plunger from a 3 ml disposable syringe and set aside. Attach the syringe barrel to the luer-lock extension of each mini-column.

3. Pipet the resin containing the bound DNA into the syringe barrel. Insert the syringe plunger and gently push the slurry into the mini-column with the syringe plunger.

4. Wash the mini-column with 2 ml of Column Wash Solution by removing the mini-column from the syringe and taking up the solution in the syringe, reattaching the syringe to the mini-column and gently pushing the column wash solution through the mini-column with the syringe plunger.

5. Remove the syringe barrel and transfer the mini-column to a microcentrifuge tube. Spin the mini-column for 2 minutes at 12,000×g to dry the resin.

6. Transfer the mini-column to a new microcentrifuge tube.

7. To elute the bound DNA, apply 50 μl of water or TE buffer to the column and wait 1 minute.

8. Spin the microcentrifuge tube containing the mini-column for 0.5–1.0 minute at 12,000×g. Remove and discard the mini-column. The isolated DNA, ready for analysis or further molecular biological procedures, may be stored in the water or TE solution in the microcentrifuge tube at 4° C. or –20° C.

EXAMPLE 5

Isolation of Single-stranded DNA From M13 Phage

This example describes a protocol for purification of single-stranded DNA (ssDNA) using the resin of Example 1 starting from 1 ml of a culture of *E. coli* infected by M13 phage.

A. Composition of Buffers

1. Column Wash Solution:
   a) 200 mM NaCl, 20 mM Tris.HCl, 5 mM EDTA, pH7.5
   b) Dilute (a) 1:1.4 with 95% ethanol.

B. Supernatant from culture of *E. coli* infected by M13 phage

1. Transfer 1.5 ml of infected culture to a microcentrifuge tube and spin for 5 min.

2. Pipette 1 ml of clarified supernatant into a new tube.

C. DNA purification using Vacuum Manifold

1. Add 1 ml of the resin of Example 1 to the supernatant from step B.2 and mix by inversion.

2. For each sample, use one mini-column. Attach a 3 ml disposable syringe barrel to the luer-lok extension of each mini-column, and insert the tip of the column assembly into the vacuum manifold.

3. Pipet the resin containing the bound DNA into the syringe barrel and pull the slurry into the mini-column by applying a vacuum. After the complete slurry volume has been drawn through the column and only the resin bed remains, turn the vacuum source off.

4. Wash the mini-column under vacuum by the addition of 2 ml Column Wash Solution to the syringe barrel.

5. Dry the resin by continuing the vacuum for an additional 0.5–2 minutes.

6. Remove the syringe barrel and transfer the mini-column to a microcentrifuge tube. Centrifuge the mini-column at top speed in a microcentrifuge for 2 minutes to remove any residual Column Wash Solution.

7. To elute the DNA, transfer the mini-column to new microcentrifuge tube. Apply 100 μl of water or TE Buffer preheated to 80° C.

8. Spin the mini-column in the microcentrifuge for 0.5–1.0 minute. Remove and discard the mini-column. The resulting DNA, ready for analysis or further molecular biological procedures, may be stored in the water or TE solution in the microcentrifuge tube at 4° C. or –20° C.

D. DNA purification using a disposal syringe (without a vacuum)

1. Add 1 ml of resin of Example 1 to the supernatant from step B.2 and mix by inversion.

2. For each sample, use one mini-column. Attach a 3 ml disposal syringe barrel to the luer-lok extension of each mini-column.

3. Pipet the resin containing the bound DNA into the syringe barrel. Insert the syringe plunger and gently push the slurry into the mini-column with the syringe plunger.

4. Wash the mini-column with 2 ml Column Wash Solution by removing the mini-column from the syringe and taking up the solution in the syringe. Reattach the syringe to the mini-column and gently push the Column Wash Solution through the mini-column with the syringe plunger.

5. Transfer the mini-column to a microcentrifuge tube, and place in a microcentrifuge. Spin the mini-column for 2 minutes to dry the resin.

6. Transfer the mini-column to a new microcentrifuge tube.

7. To elute the DNA, apply to the mini-column 100 μl of water or TE buffer preheated to 80° C.

8. Spin the microcentrifuge tube containing the mini-column for 0.5–1.0 minute in a microcentrifuge. Remove and discard the mini-column. The resulting DNA, ready for analysis or further molecular biological procedures, may be stored in the water or TE solution in the microcentrifuge tube at 4° C. or –20° C.

EXAMPLE 6

Isolation of Lambda DNA

A pellet of lambda phage obtained from a phage lysate obtained by a standard procedure is resuspended in 0.5 ml of a standard phage buffer (e.g., 150 mM NaCl, 40 mM Tris-HCl, pH 7.4, 10 mM $MgSO_4$). The resuspended phage is then transferred to a 1.5 ml microcentrifuge tube, which is centrifuged for 10 seconds at 12,000×g to remove any insoluble particles. The supernatant is drawn up, with care so as to not disturb the pellet, and transferred to a new 1.5 ml microcentrifuge tube. The supernatant is the aqueous solution of DNA (in this case packaged lambda DNA) to which the separation and isolation methods of the invention are applied. 1 ml of the suspension of Example 1 is added and mixing is carried out by inverting the tube.

If a vacuum manifold is used, follow step C.2 of Example 5. Then pipet the phage suspension into the syringe barrel and apply a vacuum to draw the suspension into the mini-column. Add 2 ml of 80% isopropanol (Column Wash Solution) to the syringe barrel, and apply a vacuum to draw this solution through the mini-column. Dry the suspension by continuing to draw a vacuum for an additional 0.5–2 minutes. Remove the syringe barrel and transfer the mini-column to a 1.5 ml centrifuge tube. Centrifuge the mini-column for 2 minutes at 12,000×g to remove any residual isopropanol solution. Transfer the mini-column to a new microcentrifuge tube. Apply 100 µl water or TE buffer preheated to 80° C. and then immediately centrifuge the mini-column for 0.5–1.0 minute at 12,000×g to elute the purified lambda DNA. Remove and discard the mini-column. The purified lambda DNA may be stored in the microcentrifuge tube at 4° C. or –20° C.

If a vacuum manifold is not used, proceed as in the previous paragraph, except use the syringe plunger to slowly and gently push the phage suspension into the mini-column, then detach the syringe from the mini-column, remove the plunger, reattach the syringe to the mini-column, pipet 2 ml of 80% isopropanol into the syringe, reinsert the plunger, and gently push the isopropanol solution through the column. Then transfer the mini-column to a 1.5 ml microcentrifuge tube and centrifuge for 2 minutes at 12,000×g to remove isopropanol solution from the resin. Transfer the column to a new microcentrifuge tube. Apply 100 µl water or TE buffer preheated to 80° C. and then immediately centrifuge the mini-column for 0.5–1.0 minute at 12,000×g to elute the purified lambda DNA. Remove and discard the mini-column. The lambda DNA may be stored in the microcentrifuge tube at 4° C. or –20° C.

EXAMPLE 7

Purification of DNA Amplified by PCR

Greater than 95% recovery can be obtained when applying between 50 ng and 16 µg of a 500 bp PCR product to 1 ml of a suspension of Example 1 or Example 2.

Percent recoveries (70–90%, for 500 bp product) using purification from low gelling/melting temperature agarose gel band slices will be lower than recoveries using direct purification (up to 95%). The agarose method is recommended when the presence of non-specific amplification products is not desirable.

Moderate recoveries can be obtained from slices of a 7M urea polyacrylamide gel. Passive elution of DNA from the gel into TE buffer over at least 30 minutes at 37° C. can be used. The DNA in the TE solution can be used as the DNA solution to which the methods of the invention are applied.

For direct purification, transfer the aqueous (lower) phase from the PCR reaction to a clean microfuge tube. Too much mineral oil in the sample can lead to a decreased yield in the PCR product purification. Aliquot 100 µl of a solution of 50 mM KCl, 10 mM Tris-HCl (pH 8.8 at 25° C.), 1.5 mM MgCl$_2$, 0.1% Triton X-100 into a 12 mm×75 mm polypropylene tube or a 1.5 ml microcentrifuge tube. Add 30–300 µl of the PCR reaction mixture. Vortex briefly to mix. Add 1 ml of the suspension of Example 1 or Example 2 and vortex briefly 3 times over a 1 minute period. Then proceed with the vacuum manifold procedure or the procedure not using a manifold, as described in Example 6 or the other examples in which such procedures are described.

EXAMPLE 8

RNA Purification

RNA may be purified by following the procedure of Example 3 and substituting the following resin for the resin given in example 1.

A 7M guanidine-HCl (i.e., guanidinium chloride) solution was prepared by dissolving 20 kg of ultrapure guanidine-HCl (Amresco Ultrapure, from Amresco, Cleveland, Ohio, USA) in 30 L of deionized distilled water.

Glass particle (i.e., in this example, glass microfiber) for the resin was then prepared as follows: Sixty-three (63) 12.5 cm glass-fiber filters, with a total mass of approximately 41.7 gms., (Whatman GF/A, Catalog No. 1820-125, widely available from Whatman through numerous distributors of laboratory and scientific apparatus) were cut into quarters. The filters were then added gradually to 6 L of 5M NaCl while dispersing with a polytron on medium to high speed. After all of the filters had been added, they were homogenized to an uniform sludge with no visible paper remaining; this homogenization lasted about 5 minutes. The sludge was then collected in a Buchner funnel and washed with about 24 L of deionized distilled water.

Although Whatman GF/A filters are specified in the instant example, Whatman GF/B, GF/C and GF/F filters are also suitable, as are any glass fiber filters having binders which are removable by the glass-microfiber preparation process described herein.

The suspension (alternatively referred to herein as a "resin" or a "slurry") was then made as follows: The 40 g of washed, glass-microfiber sludge and 900 g of silica gel 60-10 (pore size 60 Angstrom, particle size 9–11 µm, W. R. Grace, Davison Chemical Division, Baltimore, Md., USA) were added to the 30 L of 7M guanidine-HCl solution. To this solution was added 1764.6 g citrate (400 mM, pH 4.0) (Molecular Biology Grade Citric Acid, Sigma Chemical Company, St. Louis, Mo., USA).

Alternatively, a resin for RNA isolation was prepared with 0.14% (w/v) Whatman GF/A glass microfiber sludge, 4% (w/v) silica gel 60-10 in 7M guanidine hydrochloride, pH 4.0 (using 200 mM citrate buffer).

1 ml of either of these resins was used according to the procedure of Example 3 to isolate RNA.

EXAMPLE 9

RNA Purification From Tissue

This example describes RNA isolation procedures from animal tissue using a resin of Example 8.

A. Preparations for Purification

1. A 50 ml thick-walled polypropylene centrifuge tube was placed in 0.05% diethyl pyrocarbonate (DEPC) for 1 hour at room temperature and then the tube was autoclaved for 30 minutes to destroy any residual DEPC.

2. A 100 ml phenol:chloroform:isoamyl alcohol (25:24:1 v/v/v) solution was allowed to stand at room temperature for 15 minutes to allow the phases to separate.

3. A denaturing solution was prepared as follows. 25 g of guanidine thiocyanate (4M final) was added to 33 mls of CSB buffer (42 mM sodium citrate, 0.2 mM beta-mercaptoethanol and 0.83% (w/v) N-lauryl sarcosine in deionized water) and thoroughly mixed until the components completely dissolved. The denaturing solution was heated in a 65° C. water bath and stored at 4° C.

B. Tissue Disruption

To obtain optimal performance, the samples were obtained and the RNA immediately isolated. However, if the RNA is not to be immediately isolated after obtaining the sample, the sample may be frozen in liquid nitrogen and stored at –70° C. for future use.

1. 12 ml of denaturing solution was dispensed into a sterile 50 ml cell culture tube and chilled on ice for 5 minutes.

2. 1 g of tissue (either fresh or frozen) was placed into a sterile 50 ml conical cell culture tube and the denaturing solution from step B.1 was added. The tissue was disrupted with a high speed homogenizer (Brinkmann Polytron) set on high for 15–30 seconds. Alternatively, the tissue may be minced and disrupted with a Dounce glass-Teflon homogenizer.

C. RNA Extraction 1. 1.2 ml of 2M sodium acetate (pH 4.0) was added to the disrupted sample and mixed thoroughly by inversion.

2. 12 ml of the lower organic phase of the phenol:chloroform:isoamyl alcohol mixture from step A.2 was added to the sample of step C.1 and mixed by inversion. The sample was then shaken for 10 seconds and chilled on ice for 15 minutes.

3. The mixture of step C.2 was transferred to the 50 ml DEPC-treated tube (prepared in step A.1) and centrifuged at 10,000×g for 20 minutes at 4° C. Either a fixed angle or swinging bucket centrifuge may be used.

D. RNA Precipitation

1. An equal volume of isopropyl alcohol was added to the mixture of step C.3 and incubated for at least 30 minutes at −20° C., precipitating the RNA. Longer precipitations (up to overnight) should be used to precipitate RNA from samples with relatively low amounts of RNA.

2. The precipitated RNA of step D.1 was pelleted by centrifugation at 10,000×g for 15 minutes at 4° C.

3. The RNA pellet was resuspended in 5 ml of denaturing solution and vortexed until the RNA was dissolved. In some instances, heating to 65° C. may be required to resuspend the pellet. Heating should be done for as short a time as possible.

4. An equal volume of isopropyl alcohol was added to the resuspended RNA solution of step D.3 and the RNA precipitated as described in step D.1 above.

E. RNA Wash

1. The precipitated RNA of step D.4 was pelleted by centrifugation at 10,000×g for 15 minutes at 4° C. and the pellet washed with ice-cold 75% ethanol and centrifuged as above (step E.1). A minimum of 10 ml 75% ethanol should be used for this step.

2. The pellet prepared in step E.1 was dried in a vacuum desiccator for 15–20 minutes. The pellet should not be allowed to dry out completely, as this would make the RNA pellet difficult to resuspend in the next step.

3. The RNA pellet of step E.2 was resuspended in 1–3 ml of RNAase-Free Water (Promega Corp., Madison, Wis., USA), and stored at −20° C. For long term storage, the RNA should be reprecipitated by using a solution prepared as follows: A solution of sodium acetate, pH 5.0, 0.25M is prepared and added to 2.5 volumes of ethanol. Store at −70° C.

F. RNA Purification

The RNA may then be purified by utilizing 1 ml of either of the RNA resins of Example 8 and following the protocol in steps C and D of Example 3.

EXAMPLE 10

Resin Component Optimization

A control resin was prepared as in Example 1 using GF/A ground glass fiber, silica gel 60-10, and 7M guanadine hydrochloride in water. The resin had 0.35% (w/v) GF/A and 3.5% (w/v) silica gel. This resin is suitable for isolation of plasmid DNA from 100–1000 ml of culture.

This resin served as a control for a series of experiments in which the each of the ingredients was varied one at a time as the other ingredients were held constant in order to show the functional range of each of the components of the resin in isolation of DNA.

1. Variation in Silica Content of Resin

TABLE 1

| Percentage of Silica (w/v) in Experimental Resin | Approximate Average Yield of DNA Expressed as Percentage of Control Resin Yield (in %) |
| --- | --- |
| 1.25 | 80 |
| 2.5 | 90 |
| 3.125 | 98 |
| 3.5 | 150 |
| 4.375 | 165 |
| 5.0 | 170 |
| 5.625 | 155 |
| 7.5 | 90 |

2. Variation in GF/A Fiber Content of Resin

TABLE 2

| Percentage of GF/A Fiber (w/v) in Experimental Resin | Approximate Average Yield of DNA Expressed as Percentage of Control Resin Yield (in %) |
| --- | --- |
| 0.0 | 70 |
| 0.115 | 95 |
| 0.23 | 115 |
| 0.35 | 110 |
| 0.575 | 115 |
| 1.115 | 85 |

3. Variation in Guanidine Hydrochloride Molarity of Resin

TABLE 3

| Molarity of Guanidine Hydrochloride in Experimental Resin (in M) | Approximate Average Yield of DNA Expressed as Percentage of Control Resin Yield |
| --- | --- |
| 0 | 25 |
| 1 | 80 |
| 2 | 85 |
| 3 | 85 |
| 4 | 90 |
| 5 | 85 |
| 6 | 95 |
| 7 | 95 |

EXAMPLE 11

Resin Component Optimization

A control resin was prepared as in Example 1 using GF/A ground glass fiber, silica gel 60-10, and 7M guanidine hydrochloride in water. The resin had 0.14% (w/v) GF/A and 1.4% (w/v) silica gel. This resin is suitable for isolation of plasmid DNA from 1–3 mls of culture.

This resin served as a control for a series of experiments in which the each of the ingredients was varied one at a time as the other ingredients were held constant in order to show the functional range of each of the components of the resin in isolation of DNA.

1. Variation in Silica Content of Resin

TABLE 1

| Percentage of Silica (w/v) in Experimental Resin | Approximate Average Yield of DNA Expressed as Percentage of Control Resin Yield (in %) |
|---|---|
| 0.5 | 50 |
| 1 | 85 |
| 1.25 | 100 |
| 1.5 | 95 |
| 1.75 | 110 |
| 2 | 100 |
| 2.25 | 115 |

2. Variation in GF/A Fiber Content of Resin

TABLE 2

| Percentage of GF/A Fiber (w/v) in Experimental Resin | Approximate Average Yield of DNA Expressed as Percentage of Control Resin Yield (in %) |
|---|---|
| 0.05 | 65 |
| 0.1 | 75 |
| 0.15 | 80 |
| 0.25 | 85 |
| 0.5 | 75 |

3. Variation in Guanidine Hydrochloride Molarity of Resin

TABLE 3

| Molarity of Guanidine Hydrochloride in Experimental Resin (in M) | Approximate Average Yield of DNA Expressed as Percentage of Control Resin Yield |
|---|---|
| 0 | 10 |
| 1 | 75 |
| 2 | 110 |
| 3 | 85 |
| 4 | 85 |
| 5 | 105 |
| 6 | 95 |
| 7 | 95 |

The invention has been described herein with some specificity. Those of ordinary skill will recognize many modifications and variations of what has been described that remain within the spirit of the invention. It is intended that the invention encompass such modifications and variations.

We claim:

1. A mixture of silica gel and glass particles wherein the weight ratio of silica gel to the glass particles is 1:1 to 100:1.

2. A mixture of claim 1 which consists essentially of silica gel and glass microfibers.

3. A mixture of claim 1 wherein the ratio by weight of silica gel to glass particles is 5:1 to 50:1.

4. A mixture of claim 2 wherein the ratio by weight of silica gel to glass microfibers is 5:1 to 50:1.

5. A mixture of claim 1 further mixed with a chaotropic salt.

6. A mixture of claim 2 further mixed with a pe r chaotropic salt.

7. A mixture of claim 3 further mixed with a chaotropic salt.

8. A mixture of claim 4 further mixed with a chaotropic salt.

9. A mixture of any one of claims 5–8 wherein the chaotropic salt is guanidinium chloride.

10. A mixture of any one of claims 5–8 wherein the chaotropic salt is guanidinium thiocyanate.

11. A mixture of claim 10 further mixed with a chelating agent.

12. A mixture of claim 11 wherein the chelating agent is selected from the group consisting of EGTA and a soluble salt of EDTA.

13. A suspension of silica gel and glass particles in an aqueous solution wherein the weight ratio of silica gel to the glass particles is 1:1 to 100:1.

14. A suspension of claim 13 wherein the glass particles are glass microfibers.

15. A suspension of claim 13 wherein the weight ratio of silica gel to glass particles is 5:1 to 50:1.

16. A suspension of claim 14 wherein the weight ratio of silica gel to glass particles is 5:1 to 50:1.

17. A suspension of claim 13 wherein, in the solution, guanidinium ion is present at a concentration of at least 4M.

18. A suspension of claim 14 wherein, in the solution, guanidinium ion is present at a concentration of at least 4M.

19. A suspension of claim 15 wherein, in the solution, guanidinium ion is present at a concentration of at least 4M.

20. A suspension of claim 16 wherein, in the solution, guanidinium ion is present at a concentration of at least 4M.

21. A suspension of claim 17 wherein the chaotropic salt is guanidinium hydrochloride at a concentration of 6M to 8M.

22. A suspension of claim 18 wherein the chaotropic salt is guanidinium hydrochloride at a concentration of 6M to 8M.

23. A suspension of claim 19 wherein the chaotropic salt is guanidinium hydrochloride at a concentration of 6M to 8M.

24. A suspension of claim 20 wherein the chaotropic salt is guanidinium hydrochloride at a concentration of 6M to 8M.

25. A suspension of claim 17 wherein the chaotropic salt is guanidinium thiocyanate at a concentration of 5M to 7M.

26. A suspension of claim 18 wherein the chaotropic salt is guanidinium thiocyanate at a concentration of 5M to 7M.

27. A suspension of claim 19 wherein the chaotropic salt is guanidinium thiocyanate at a concentration of 5M to 7M.

28. A suspension of claim 20 wherein the chaotropic salt is guanidinium thiocyanate at a concentration of 5M to 7M.

29. A suspension according to any of claims 24–28 which comprises EGTA or a salt of EDTA.

30. A suspension according to claim 29 which comprises the disodium salt of EDTA at a concentration between about 5 mM and about 15 mM.

* * * * *

UNITED STATES PATENT AND TRADEMARK OFFICE
CERTIFICATE OF CORRECTION

PATENT NO. : 5,658,548
DATED : August 19, 1997
INVENTOR(S) : Vikas V. Padhye, et al.

It is certified that error appears in the above-indentified patent and that said Letters Patent is hereby corrected as shown below:

In column 14, line 41 of the patent, delete "$\leqq 300$" and insert in its place --$\leq 300$--

In column 22, line 1 of the patent, delete "pe r 5"

Signed and Sealed this

Twenty-third Day of March, 1999

Attest:

Q. TODD DICKINSON

*Attesting Officer*      *Acting Commissioner of Patents and Trademarks*

(12) REEXAMINATION CERTIFICATE (4401st)
United States Patent
Padhye et al.

(10) Number: US 5,658,548 C1
(45) Certificate Issued: Jul. 24, 2001

(54) NUCLEIC ACID PURIFICATION ON SILICA GEL AND GLASS MIXTURES

(75) Inventors: Vikas V. Padhye; Chuck York, both of Madison, WI (US); Adam Burkiewicz, Gdansk (PL)

(73) Assignee: Promega Corporation, Madison, WI (US)

Reexamination Request:
No. 90/005,242, Jan. 27, 1999

Reexamination Certificate for:
Patent No.: 5,658,548
Issued: Aug. 19, 1997
Appl. No.: 08/476,849
Filed: Jun. 7, 1995

Certificate of Correction issued Mar. 23, 1999.

Related U.S. Application Data

(63) Continuation-in-part of application No. 08/115,504, filed on Aug. 30, 1993, now abandoned.
(51) Int. Cl.[7] .............................. C03C 1/00; C03C 12/00; C01B 33/12; C01B 33/14
(52) U.S. Cl. ..................... 423/335; 536/25.42; 435/91.1; 428/406
(58) Field of Search ..................... 423/335; 536/25.42, 536/25.4, 25.41; 435/91.1; 428/406; 501/32

(56) References Cited

U.S. PATENT DOCUMENTS 5,401,466  3/1995  Foltz et al. .

FOREIGN PATENT DOCUMENTS 5 2147 598   12/1977   (JP) .

*Primary Examiner*—Gary L. Kunz

(57) ABSTRACT

The present invention provides compositions and methods for isolating nucleic acids with lengths greater than about 50 bases, from cells, gels, solutions and other media, in which nucleic acids occur in vivo or in vitro. The compositions of the invention are mixtures of the silica materials silica gel and glass particles, particularly glass microfibers; such mixtures combined with chaotropic salts, such as guanidinium chloride or guanidinium thiocyanate; and suspensions of such mixtures in aqueous solutions of chaotropic salts. In the methods of the invention, an aqueous solution comprising nucleic acid is mixed with an aqueous solution of chaotropic salts and the resulting solution is contacted with a mixture of the silica materials, whereupon the nucleic acid in the solution binds to the silica materials. The chaotropic salts and components, other than the nucleic acid adsorbed to the silica materials, from the aqueous solution treated by the method of the invention are washed from the silica materials. Finally, the nucleic acid can be obtained by elution from the silica materials. The methods provide nucleic acid in water or buffer, such as TE buffer, free of contamination by any salt or macromolecule that would interfere with further processing or analysis.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 13–30 is confirmed.

Claims 1–4 are cancelled.

Claims 5–8 are determined to be patentable as amended.

Claims 9–12, dependent on an amended claim, are determined to be patentable.

5. A mixture [of claim 1] *for use in isolating nucleic acids, comprising silica gel and glass particles* further mixed with a chaotropic salt, *wherein the weight ratio of the silica gel to the glass particles is 1:1 to 100:1 and wherein the mixture is capable of preferentially isolating nucleic acid fragments of greater than about 50 bases in length.*

6. A mixture [of claim 2] *for use in isolating nucleic acids, consisting essentially of silica gel and glass microfibers* further mixed with a chaotropic salt, *wherein the weight ratio of the silica gel to the glass microfibers is 1:1 to 100:1 and wherein the mixture is capable of preferentially isolating nucleic acid fragments of greater than about 50 bases in length.*

7. A mixture [of claim 3] *for use in isolating nucleic acids, comprising silica gel and glass particles* further mixed with a chaotropic salt, *wherein the weight ratio of the silica gel to the glass particles is 5:1 to 50:1 and wherein the mixture is capable of preferentially isolating nucleic acid fragments of greater than about 50 bases in length.*

8. A mixture [of claim 4] *for use in isolating nucleic acids, consisting essentially of silica gel and glass microfibers* further mixed with a chaotropic salt, *wherein the weight ratio of the silica gel to the glass microfibers is 5:1 to 50:1 and wherein the mixture is capable of preferentially isolating nucleic acid fragments of greater than about 50 bases in length.*

* * * * *